US010525286B2

(12) United States Patent
Fagerstrom et al.

(10) Patent No.: US 10,525,286 B2
(45) Date of Patent: Jan. 7, 2020

(54) COMPACT SHARPENING FILTER FOR ORTHOVOLTAGE X-RAYS

(71) Applicant: Wisconsin Alumni Research Foundation, Madison, WI (US)

(72) Inventors: Jessica Fagerstrom, Edmonds, WA (US); Edward Bender, Madison, WI (US); Wesley Culberson, Madison, WI (US); Michael Lawless, Madison, WI (US); Benjamin R. M. Palmer, Madison, WI (US); Larry DeWerd, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 425 days.

(21) Appl. No.: 15/598,716

(22) Filed: May 18, 2017

(65) Prior Publication Data

US 2018/0333592 A1 Nov. 22, 2018

(51) Int. Cl.
*A61N 5/10* (2006.01)
*G21K 3/00* (2006.01)

(52) U.S. Cl.
CPC .... *A61N 5/1077* (2013.01); *A61N 2005/1091* (2013.01); *A61N 2005/1095* (2013.01)

(58) Field of Classification Search
CPC .... A61N 2005/1091; A61N 2005/1095; A61N 5/1077; A61B 6/06; A61B 6/487; A61B 6/542; A61B 6/12; A61B 6/548; A61B 6/4035; A61B 6/032; A61B 6/482; A61B 6/035; A61B 6/4042; A61B 6/583; A61B 6/02; A61B 6/504; A61B 2576/023; A61B 5/0066; A61B 5/0084; A61B 5/02007; A61B 5/7289; A61B 5/7292; G21K 1/10; G21K 1/04; G21K 1/025; G21K 1/043; G21K 1/02; G21K 1/062; G21K 2201/067; G06T 2207/30101; G06T 7/70; A61M 25/104
USPC .............................. 378/65, 62, 64, 147–160
See application file for complete search history.

(56) References Cited

U.S. PATENT DOCUMENTS

| | | | | |
|---|---|---|---|---|
| 5,204,888 A | * | 4/1993 | Tamegai | A61B 6/4035 378/156 |
| 5,369,678 A | * | 11/1994 | Chiu | A61B 6/06 378/152 |
| 5,684,851 A | * | 11/1997 | Kurbatov | G01N 23/046 378/149 |
| 6,501,828 B1 | * | 12/2002 | Popescu | A61B 6/06 378/145 |
| 6,535,837 B1 | * | 3/2003 | Schach Von Wittenau | A61N 5/1031 378/64 |
| 8,571,178 B2 | * | 10/2013 | Sendai | A61B 6/4042 378/157 |
| 8,761,347 B2 | * | 6/2014 | Brown | A61N 5/1048 378/156 |
| 8,971,491 B2 | | 3/2015 | Bender | |

(Continued)

*Primary Examiner* — Irakli Kiknadze
(74) *Attorney, Agent, or Firm* — Boyle Fredrickson S.C.

(57) ABSTRACT

A sharpening filter for orthovoltage x-ray beams employs a substantially planar filter disk supporting a set of radial symmetric features controlling attenuation of x-ray transmission in concentric circular regions providing increased sharpness of the pencil beams in a compact filter structure that may be tailored to different beam sizes and focus depths.

18 Claims, 6 Drawing Sheets

(56) References Cited

U.S. PATENT DOCUMENTS 9,498,646 B2    11/2016   Bender et al.

\* cited by examiner

COMPACT SHARPENING FILTER FOR ORTHOVOLTAGE X-RAYS

STATEMENT REGARDING FEDERALLY SPONSORED RESEARCH OR DEVELOPMENT

—

CROSS REFERENCE TO RELATED APPLICATION

—

BACKGROUND OF THE INVENTION

The present invention relates to orthovoltage x-ray machines for radiation therapy and in particular to a filter for improving the sharpness of radiation beams generated by such machines.

Many stereotactic radiosurgery (SRS) and stereotactic body radiation therapy (SBRT) treatments require highly conformal dose distributions with sharp dose gradients at the target periphery. Delivering a more homogeneous dose to the target volume has been associated with reduced adverse effects and toxicities. Delivering a precise dose to the target volume also allows for the prescription to a higher isodose volume without excessive dose to nearby critical structures.

One method for achieving sharp dose distributions is through modulation of the SRS beam combined with the use of low energies. Previous work with 6 megavolt SRS pencil beams has used sets of concentric hypodermic tubing of varying lengths and diameters inserted into standard SRS cone collimators to increase profile uniformity within the irradiated volume, as well as to increase the steepness of the dose gradient on the periphery. See E. T. Bender, "Increasing dose gradient and uniformity in small fields using modulation: theory and prototypes for cone-based stereotactic radiosurgery," Med. Phys. 41, 5, 051706-1-051706-7525 (2014) hereby incorporated by reference.

The sharpness of the pencil beam's dose gradient is defined by a combination of geometric penumbra and radiologic penumbra. The geometric penumbra is caused by the finite size of the x-ray focal spot of the x-ray tube interacting with the edges of a downstream collimator. Generally, the smaller the x-ray focal spot and the closer the collimation to the treatment volume, the smaller the geometric penumbra. The radiologic penumbra is caused by scattering within the tissue of the patient and is largely indifferent to the geometry of the x-ray system.

For standard SRS fields, the radiological penumbra is the dominating component of the overall penumbra. Reduction of beam energy from the standard megavoltage range into the orthovoltage energy range offers a dosimetric benefit by reducing the range of the secondary electrons generated by the x-rays and thus shrinking the radiological penumbra. Unfortunately, the focal spot sizes for orthovoltage units are larger than those for standard 6 MV linear accelerators increasing the geometric penumbra. This geometric penumbra may be minimized to some extent by the use of collimators near the volume to be irradiated.

SUMMARY OF THE INVENTION

The present invention provides a sharpening filter for orthovoltage x-ray beams (200 kVp-500 kVp) providing improved operation, versatility, or manufacturability. The filter uses an axially compact filter plate having concentric circular attenuation regions to produce the necessary sharpening effect. The substantially flat form factor of the filter allows the filter to be easily installed and replaced, and the concentric circular attenuation regions are amenable to computerized optimization of the region sizes and spacing.

Specifically, the invention provides a sharpening filter for orthovoltage x-rays including a collimator providing a central channel extending along an axis between an inlet and an outlet, the collimator receiving x-rays from an orthovoltage x-ray source at the inlet and collimating those x-rays into a collimated beam. A filter plate is positioned within the beam providing at least a first and second circular attenuation region within the beam and concentric about the axis. The first and second circular attenuation regions provide different axial x-ray attenuations, which serves to sharpen the periphery of the beam at a treatment plane spaced from the filter plate in the direction of x-ray propagation.

It is thus a feature of at least one embodiment of the invention to provide a compact and easily manufactured filter that can be used to sharpen beam dose delivery.

The circular attenuation regions may have a radial thickness of no less than 0.5 millimeters. In some embodiments, the filter plate provides less than four concentric circular attenuation regions each providing different axial x-ray attenuations.

It is thus a feature of at least one embodiment of the invention to provide a readily manufactured filter element providing simply fabricated structures that can offer significant beam transmission variations for significant sharpness improvement.

In one embodiment, the filter maybe composed of metal or a metal composite.

It is thus a feature of at least one embodiment of the invention to permit use of a wide range of manufacturing techniques from printing to casting to injection molding or machining to produce the necessary filters.

In one embodiment, the filter may be attached at the outlet of collimator.

It is thus a feature of at least one embodiment of the invention to provide a filter that can be easily installed and removed from a collimator block.

The invention may be used to produce a kit of sharpening filters for orthovoltage x-ray beams, providing a set of collimators and interchangeable filter plates, as described above, to sharpen beams of different diameters and different filter-to-treatment area distances.

It is thus a feature of at least one embodiment of the invention to provide a filter system that can be readily intermixed with collimator blocks to provide the clinician with a wide range of filtration options.

The simplified design of the filter of the present invention, employing a limited number of discrete radially symmetric zones, lends itself to optimization using computerized methods. The invention also provides a method of optimizing filters of this design using the steps of: (a) employing a genetic algorithm to generate a set of potential filters providing the radial features described above; (b) modeling the collimated beam produced by each of the sets of filters at the treatment plane; (c) assessing the fitness of each of the collimated beams according to the sharpness of the dose distribution at the desired treatment plane; (d) returning the fitness information to the genetic algorithm to produce a new set of filter designs combining features of the best filters; and (e) repeating steps (a)-(d) for multiple iterations to produce at least one filter design that improves sharpness.

It is thus a feature of at least one embodiment of the invention to provide a simple filter design having a constrained design space optimizable by algorithmic means.

These particular objects and advantages may apply to only some embodiments falling within the claims and thus do not define the scope of the invention.

BRIEF DESCRIPTION OF THE DRAWINGS

FIG. 1 is a fragmentary perspective view of an example orthovoltage x-ray beam positioned to irradiate a patient or phantom, to produce an orthovoltage x-ray beam for treating a tumor or the like;

DETAILED DESCRIPTION OF THE PREFERRED EMBODIMENT

Figure 1:
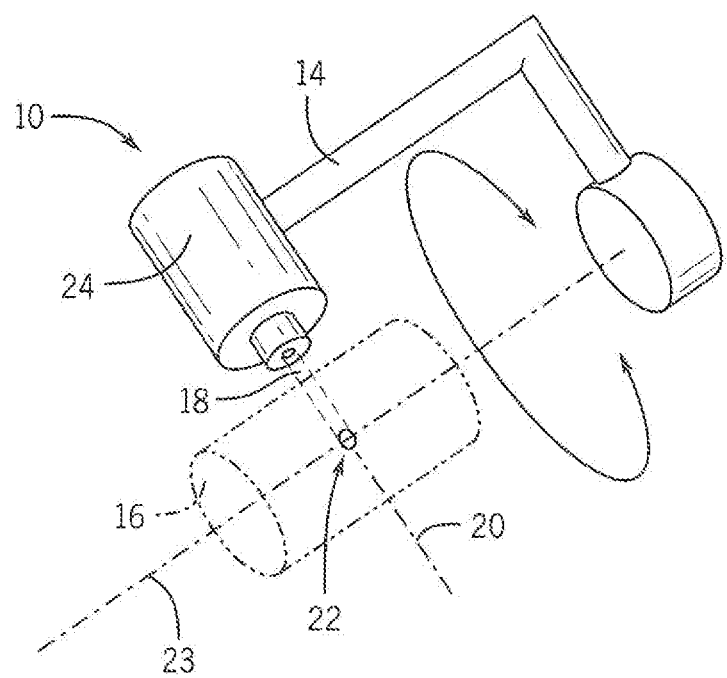

Referring now to FIG. 1, the filter of the present invention may be used in orthovoltage x-ray system 10 providing an x-ray source assembly 12 positionable, for example, on a gantry arm 14 with respect to a patient, phantom, or research subject 18, for stereotactic radiotherapy. Generally, x-ray source assembly 12 may generate a collimated beam 18 of orthovoltage x-rays in the range of 200-500 kVp to be delivered along a treatment axis 20 to a treatment region 22, for example, the latter being positioned at a treatment plane 23 and centered at an iso-center of motion of the x-ray source assembly 12 on the gantry arm 14.

Figure 2:
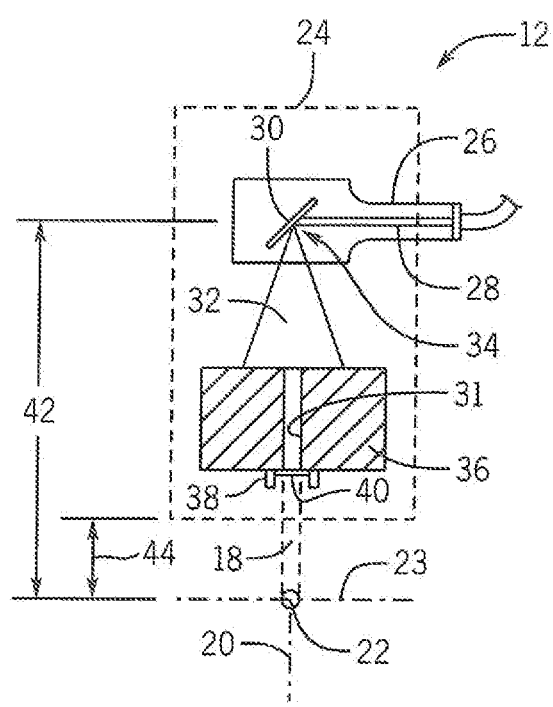
FIG. 2 is a schematic diagram of the orthovoltage x-ray system of FIG. 1 showing an x-ray tube and collimation assembly including a filter of the present invention.

Referring now to FIG. 2, the x-ray source assembly 12 may include a housing 24 supporting an x-ray tube 26 of conventional design. X-ray tube 26 may accelerate a beam of electrons 28 into a target 30 to produce an un-collimated x-ray beam 32 centered along the axis 20 and emanating from a focal spot 34 on the target 30. The size of the focal spot 34 will generally depend on the x-ray tube 26 and its operating parameters and affects the sharpness of the collimated beam 18. In one embodiment, the focal spot may be 5.5 millimeters in diameter.

The un-collimated x-ray beam 32 projecting from the x-ray tube 26 along axis 20 may be received by a block collimator 36, for example, constructed of an x-ray absorbing material such as leaded brass alloy. The block collimator 36 has a thickness along the axis 20 to substantially block the un-collimated x-ray beam 32 except along a cylindrical channel 31 cut through the block collimator 36 along the axis 20. The un-collimated x-ray beam 32 passes into an inlet of the channel 31 that produces a collimated beam 18 that exits from an outlet of the channel 31. In one embodiment, a source-to-axis distance 42 between the focal spot 34 and the isocenter of the treatment region 22 may be approximately 100 centimeters.

In one embodiment, the block collimator 36 may have a dimension of 9 by 10 by 3.175 centimeters. Generally, the invention contemplates that multiple block collimators 36 may be interchanged within the housing 24 each defining a different diameter of a collimated beam 18, for example, providing channel 31 diameters of that produce collimated beams 18 that have nominal widths of 5, 6, 8, and 10 millimeters at the treatment region 22.

A plate-like filter disk 40 may be affixed to the block collimator 36 to attenuate the collimated beam 18, for example, as shown, on the outlet of the channel 31 and centered along the axis 20. The filter disk may be located and retained by centering elements 38 allowing placement of different filter disks 40 on a given block collimator 36 to optimize for different filter-to-treatment zone distances 44 between the filter disk 40 and the treatment region 22. The filter-to-treat zone distance 44 may be kept constant within a range of 70 to 115 centimeters, with a treatment depth within a range of 2.5 to 7.5 centimeters in target material. The centering elements 38 may, for example, be any mechanical attachment mechanism including machine screws and a collar or the like.

Referring now to FIGS. 3-6, the filter disk 40 will generally provide an active region 46 within a diameter 48 of the channel 31 of the block collimator 36 on which it is centered. This active region will position one or more concentric circular attenuation regions 50 about the axis 20 within the collimated beam 18. Each attenuation region 50 will be defined by an association with a different axial attenuation of x-rays passing axially therethrough (i.e., along axis 20).

Each attenuation region 50 will provide a circular feature centered on the axis 20 either being cylindrical (for the centermost region) in the form of a hole or pillar or the like or annular for regions outside of the centermost region. Each attenuation region 50 provides an increased or decreased axial thickness of the filter disk 40 with respect to its neighbors (for a homogenous filter disk 40) or materials of greater or lesser attenuation (when the filter disk 40 is constructed of multiple different materials). The dimensions of particular attenuation regions will depend on the diameter 48 of the pencil beam 18, the depth of treatment 44 (shown in FIG. 2) and the geometry of the x-ray source assembly 12 with respect to the size of the focal spot 34 and its distance along the axis 20 to the filter disk 40.

Figure 3:
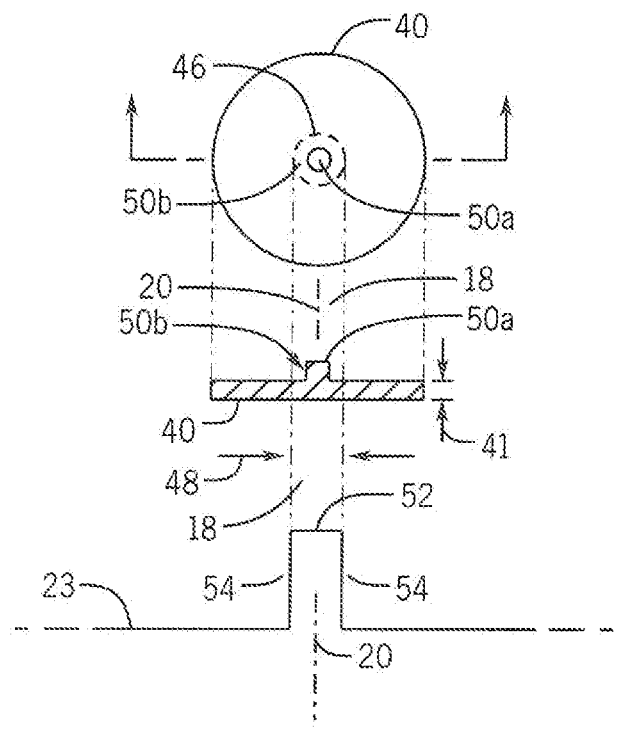
FIG. 3 is a first example filter shown in top plan view and side elevational view aligned along a common axis with a simplified dose profile of the filter at a treatment plane for a five-millimeter collimated beam.

In one embodiment shown in FIG. 3, for the x-ray source assembly 12 of FIG. 2 and a channel diameter of five-millimeters, a single central pillar forms the centermost attenuation region 50a providing a higher attenuation than a surrounding annular attenuation region 50b, the latter having an axial thickness 41 equal to the axial base thickness of the filter disk 40 of approximately 0.5 millimeters in one embodiment. In one embodiment, the central pillar may be approximately 2.5 millimeters in axial height and one millimeter in diameter.

Figure 4:
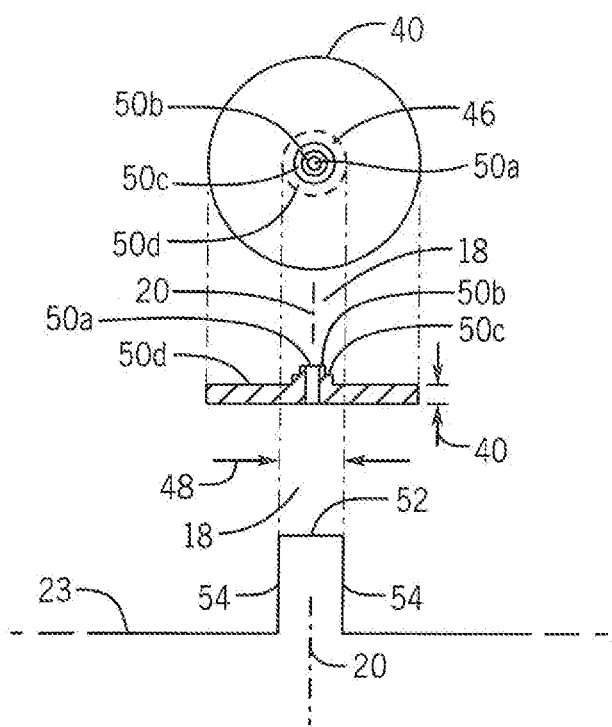
FIG. 4 is a second example of a filter similar to FIG. 3 for a six-millimeter collimated beam.

In a second embodiment shown in FIG. 4, for the x-ray source assembly 12 of FIG. 2 and for a channel diameter of six-millimeters, the single central pillar may be replaced by a single central aperture attenuation region 50a passing through the filter disk 40. Surrounding this aperture attenuation region 50a is a first ring of increased axial thickness providing attenuation region 50b and a second ring of increased axial thickness (but less axial thickness than attenuation region 50b) providing attenuation region 50c. Finally, attenuation region 50c is surrounded by a lower attenuation region 50d being essentially this nominal thickness of the filter disk 40 of approximately 0.5 millimeters. The aperture of attenuation region 50a may be approximately 1 millimeter in diameter. Attenuation region 50b may be approximately 1.5 millimeters in axial height, and attenuation region 50c may be approximately 1 millimeter in axial height, with each radial wall thickness approximately 0.5 millimeters.

Figure 5:
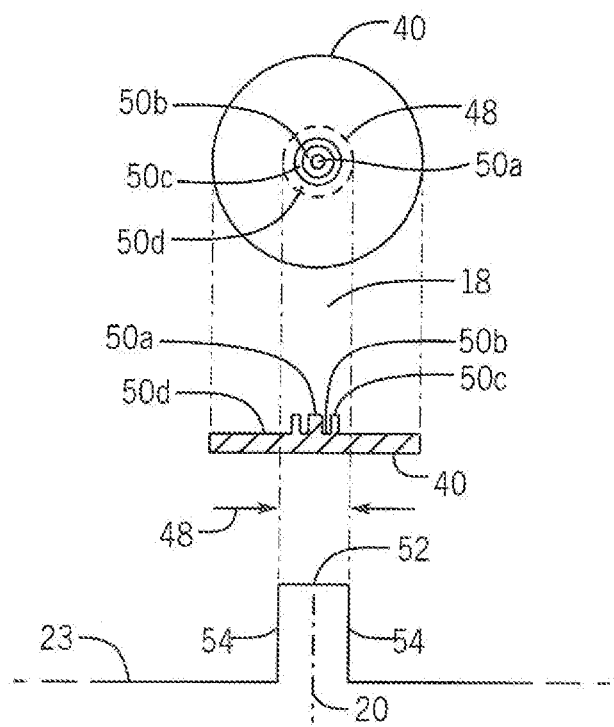
FIG. 5 is a third example of a filter similar to the filters of FIGS. 3 and 4 for an eight-millimeter collimated beam.

In a third embodiment, shown in FIG. 5 for the x-ray source assembly 12 of FIG. 2 for channel diameter of 8 millimeters, the central attenuation region 50a may be a pillar extending axially from the surface of the filter disk 40 surrounded by an annular moat forming attenuation region 50b and having the nominal axial thickness of 0.5 millimeters of the filter disk 40. This attenuation region 50b may be surrounded in turn by an attenuation region 50c of increased thickness which is then finally surrounded by yet another reduced attenuation region providing attenuation region 50d equal substantially to the thickness of the filter disk 40 of 0.5 millimeters. The central pillar of attenuation region 50a may have a diameter (measured perpendicularly to axis 20) of one millimeter and a height (measured along axis 20) of approximately 0.5 millimeters in the attenuation region 50c and may have a radial wall thickness (measured perpendicularly to axis 20) of approximately one millimeter and inside radius (measured perpendicularly to axis 20) of approximately one millimeter.

Figure 6:
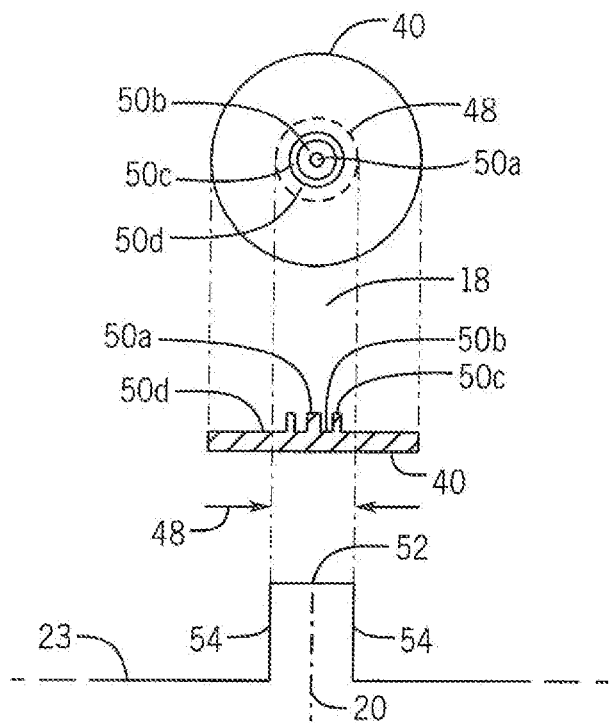
FIG. 6 is a figure similar to that of FIGS. 3, 4, and 5 of an example filter for a ten-millimeter collimated beam.

This pattern of the attenuation regions 50 of the third embodiment may be expanded as shown in FIG. 6 for the x-ray source assembly 12 of FIG. 2 for a channel diameter of ten-millimeters. As with the embodiment of FIG. 5, the first attenuation region 50a provides a pillar surrounded by a moat forming the attenuation region 50b, surrounded by an annular wall extending axially from the filter disk 40 forming attenuation region 50c in turn surrounded by attenuation region 50d being substantially the nominal thickness of the filter disk 40. The central pillar of attenuation region 50a may have a diameter of one millimeter and a height of 1.5 millimeters and the attenuation region 50c may have a radial wall thickness of 0.5 millimeters and an inside radius of 1.5 millimeters.

Generally, the filter disk 40 may be modified to include either holes through the filter disk 40 (for example, shown in FIG. 4) or built up concentric circular regions having a height from 0.5 millimeters to five-millimeters. The material of the filter disk 40 may be any attenuating material but in one embodiment is a tungsten composite that may be constructed by additive machining processes, for example, binderjetting such as may be used to create epoxy-infiltrated tungsten parts. Alternatively, the filter disk 40 may be constructed by casting, using a curing epoxy, or injection molding using a thermoplastic polymer infused with tungsten or other metal particles. In one embodiment, the filter material may have a density of 11.206 g/cm$^3$ with a composition, by weight, of 4.08% organic material and 95.92% tungsten. The invention further contemplates the filters 40 can be constructed by conventional machining techniques, for example, using a metalworking lathe or milling machine operating on a composite or solid metal material.

Referring still to FIGS. 3-6, x-rays passing through the filter disks 40 provide a collimated beam 18 having a beam profile 52 measured at a treatment plane 23 with improved characteristics. As is understood in the art, beam profile 52 indicates dose as a function of distance perpendicular to the axis 20. While the applicants do not wish to be bound by a particular theory, it is believed that these concentric attenuation regions operate to create a summation of periodic functions to modify the beam profile 52 to provide a greater sharpness (dose gradient) to the peripheral regions 54 of the beam profile 52 reflecting a reduced penumbra. The particular dimensions that optimize the filter disks 40 will depend on the diameter of the channel 31, the energy level of the orthovoltage x-rays, the size of the focal spot 34, and the relative separations between the focal spot 34, the block collimator 36, the filter disk 40 and the iso-centric treatment region 22.

Figure 7:
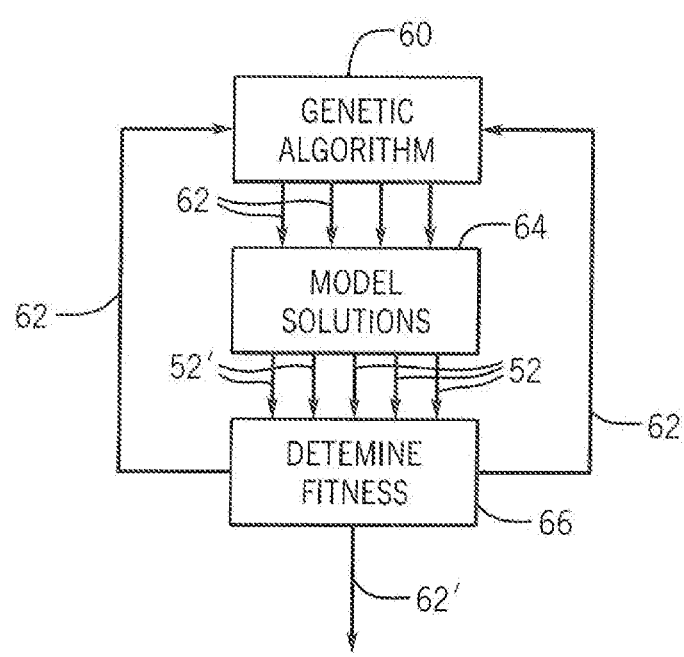
FIG. 7 is a block diagram of a design process for optimizing the filters of FIGS. 3-6.
Figure 8A:
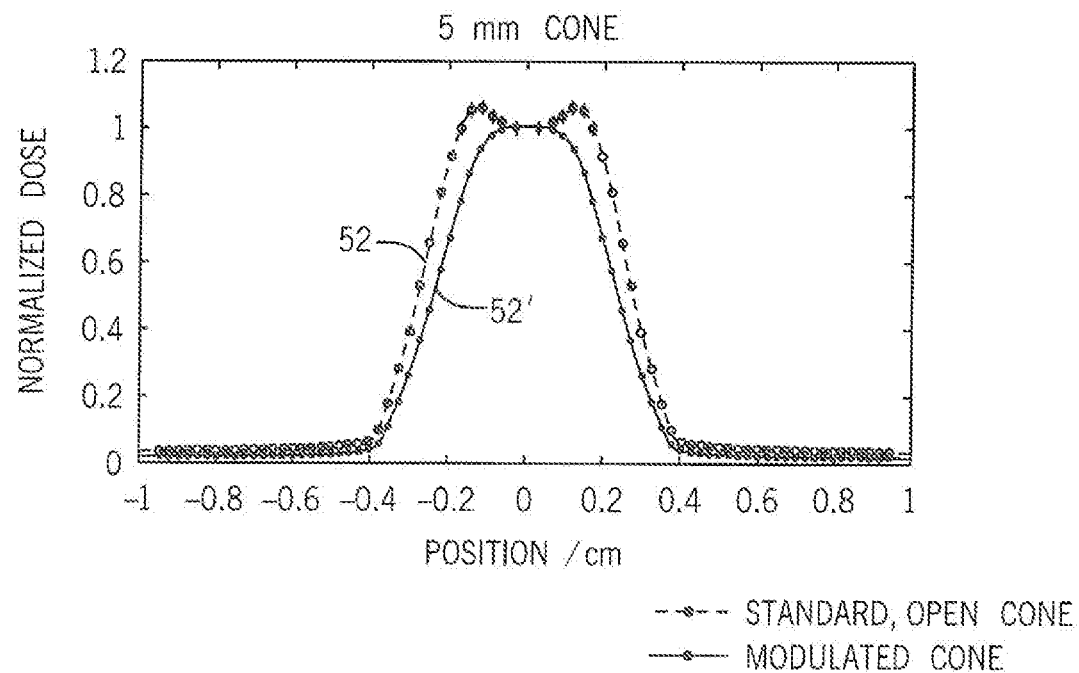
FIGS. 8a-8d are dose profiles corresponding respectively to the filters of FIGS. 3-5 showing a dose profile produced without the filter in place and with the filter in place, the latter providing improved sharpness (steepness) in the peripheral dose regions.
Figure 8B:
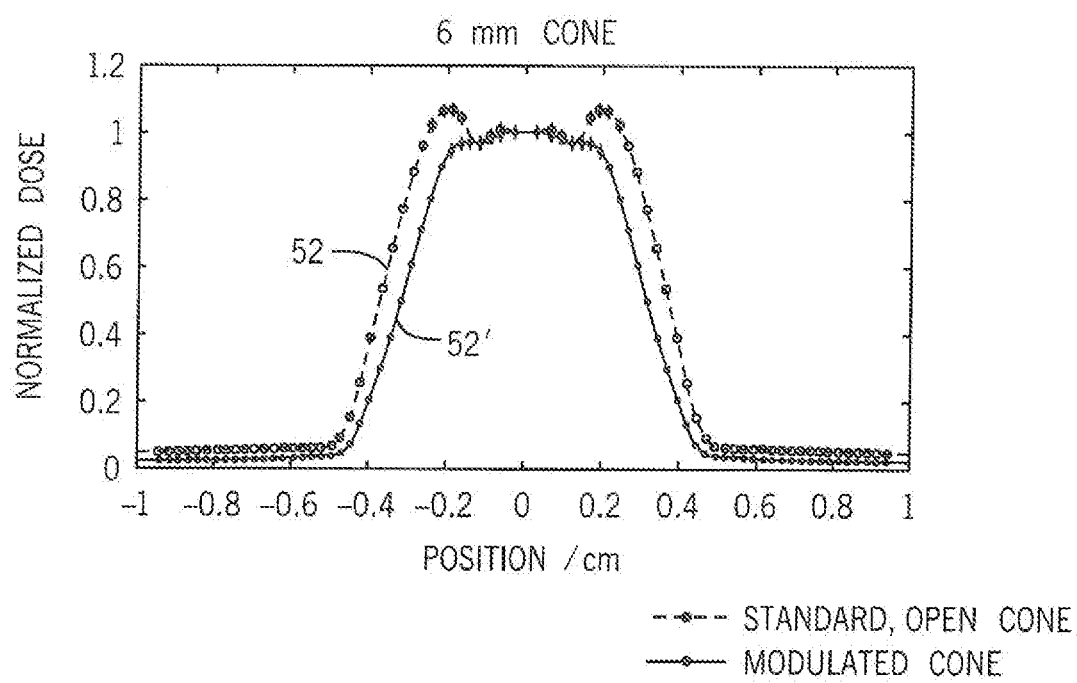
Figure 8C:
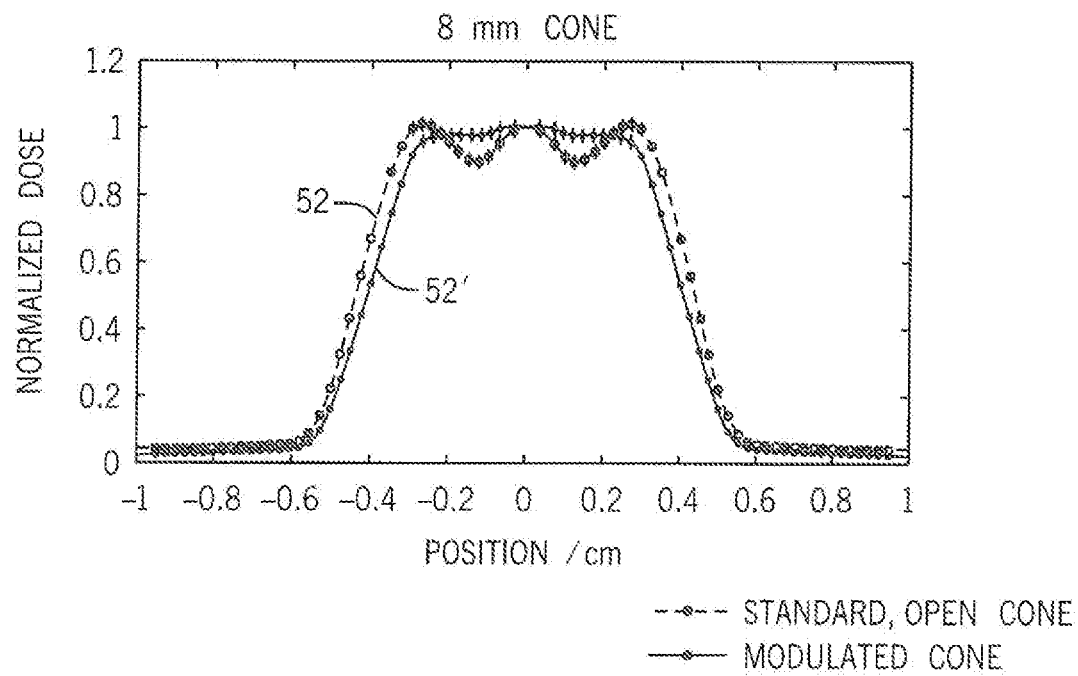
Figure 8D:
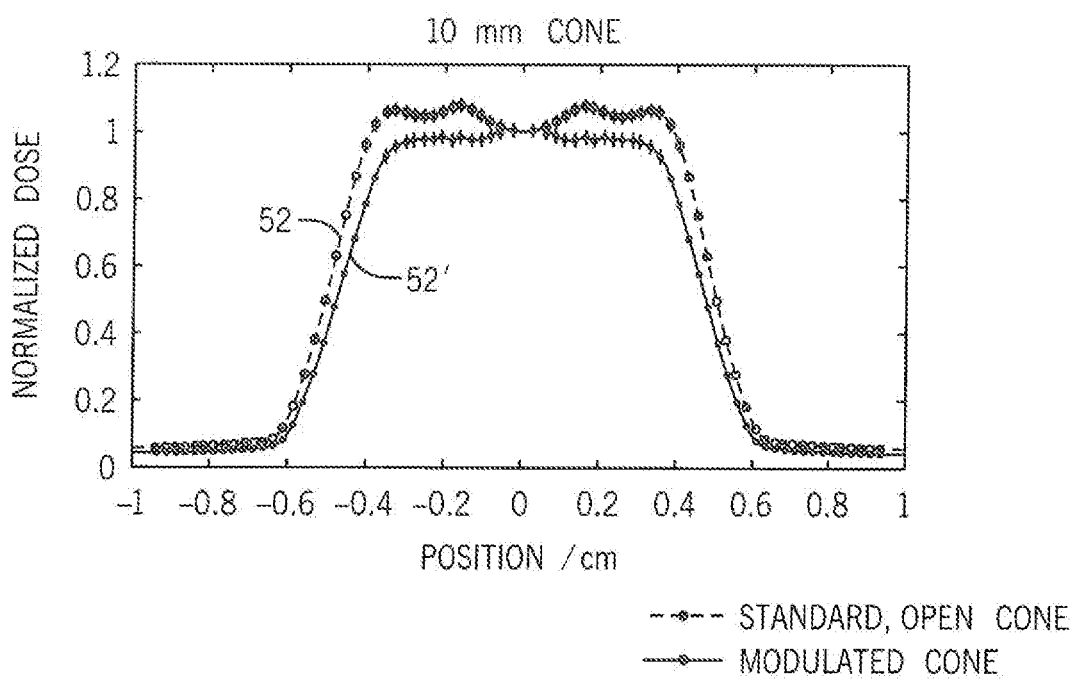

Referring now to FIG. 7, in the preferred embodiment, the dimensions of the filter disk 40 may be determined by an optimization program varying the dimensions of the attenuation regions 50 and modeling the results to obtain desired beam profiles 52. In one embodiment, the determination of optimal dimensions for the filter disk 40 may make use of a "genetic algorithm," for example, of the type described in: J. H. Holland, "Adaptation in natural and artificial systems: an introductory analysis with applications to biology, control, and artificial intelligence", (The MIT Press, Cambridge, Mass., 1975) hereby incorporated by reference. Using the genetic algorithm, a population of potential solutions evolves iteratively under predetermined constraints. Because genetic algorithms are able to minimize objective functions that are not smooth, they may be better suited for this problem better than gradient-search methods. This genetic algorithm, indicated by process block 60, may accept seed designs or randomly generate a number of initial designs 62 for filter disks 40, each design characterized by a set of dimensions of attenuation regions 50 and a number of attenuation regions 50 of the particular filter disk design. The variations among the filter disks 40 at this and subsequent iterations may be constrained to limit the optimization space. For example, the attenuation regions 50 of each filter disk 40 must have radial symmetry about the axis 20 and have height, diameter, and radial thickness ranges that vary only in increments of 0.5 millimeters within the range of the collimated beam diameter. The number of discrete radial features may also be limited, for example, to less than five attenuation regions. The maximum height of the features of the attenuation regions 50 may also be limited, for example, to less than five-millimeters.

The performance of these design filter disks 40 is then modeled to provide a corresponding set of beam profiles 52 as indicated by process block 64 for each of the design filter disks 40. In addition, a baseline beam profile 52' for the x-ray source assembly 12 without any filter disk 40 may be determined.

Each modeled beam profile 52, as discussed above, will provide an x-ray dose at various points in a volume D(x, y, z). The beam profiles 52 may be generated for each filter disk 40 by any radiation dose simulation techniques known in the art for modeling radiation dose based on the particular geometry and components of the x-ray source assembly 12 determined by calculation or by empirical measurements. In one embodiment, the simulation can be implemented using a Monte Carlo system, EGSnrc, using the code, BEAMnrc, with the FLATFILT component module, available from the National Research Council of Canada.

As indicated by process block 66, the beam profiles 52 may be analyzed to determine the fitness of each beam profile 52 according to an objective function, for example, comparing the beam profiles 52 of each design filter disk 40 to a desired, ideal dose, for example, a rectangular function providing an infinitely sharp boundary at the periphery of the beam profile 52. For example, the objective function may be a sum of the squares of the differences between the simulated beam profile 52 (at the treatment plane 23) and a rectangular function dose distribution. This analysis may be performed, for example, using the built-in GA function of MATLAB (commercially available from MathWorks of Natick, Mass.) in the Global Optimization toolbox of that program or other similar tools well known in the art.

These fitness values determined at process block 66 may be further modified by a weighting indicating the total fluence that passed through the designed filter disk 40 so as to bias the filter design toward filters that allow greater transmission of x-ray fluence.

Referring still to FIG. 7, the fitness values associated with each design filter disk 40 may be used to select particular design filter disks 40 to return to the genetic algorithm for an additional iteration. These returned design filter disks 40 are then "bred" to create new design filter disks 40 for additional iterations.

After a given predetermined number of iterations after a design filter disk 40 satisfies a predetermined fitness level, that filter design 62 and the details of its construction may be output as the best filter designs 62'. This time the fitness value of the best filter design 62' and its comparison to the beam profile 52' of a non-filtered beam 18 may also be output.

The design description of the filter disk 40 having the best filter design 62' may then be used to construct actual filter disks 40, for example, by machining, printing, or the creation of a pattern for casting or injection mold making. These filters may then be used on an x-ray source assembly 12.

The limited and well-defined parameters of the filter disks 40 of the present invention, providing a limited set of radial features characterized by discrete steps of thickness, diameter, and radial thickness, lend themselves to a wide variety of machine optimization techniques and accordingly the invention contemplates that the genetic algorithm described may be replaced with other optimization techniques such as simulated annealing and the like.

Referring now to FIGS. 8a-8d, comparison of the beam profiles 52 (with the corresponding filter disk 40 in place) and beam profiles 52' (without any filter disk 40) for each of five-millimeter, six-millimeter, eight-millimeters, and ten-millimeter channel diameters of channel 31 produced by the present invention for the x-ray source assembly 12 of FIG. 2 shows improved sharpness at the periphery of the dose profiles 52. The following table tabulates these differences quantitatively.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A sharpening filter for orthovoltage x-rays comprising:
    a collimator providing a central channel extending along an axis between an inlet and an outlet, the collimator receiving x-rays from an orthovoltage x-ray source at the inlet and attenuating those x-rays into a collimated beam; and
    a filter plate positioned within the collimated beam providing at least a first and second circular attenuation region within the collimated beam and concentric about the axis, the at least first and second circular attenuation

TABLE 1

| | | 80%-20% penumbra | | | 90%-10% penumbra | | |
|---|---|---|---|---|---|---|---|
| Cone Size (mm) | depth (cm) | standard (mm) | modulated (mm) | percent decrease | standard (mm) | modulated (mm) | percent decrease |
| 5 | 2.5 | 1.483 | 1.245 | 16 | 2.154 | 1.825 | 15 |
| 6 | 2.5 | 1.499 | 1.278 | 15 | 2.114 | 1.897 | 10 |
| 8 | 2.5 | 1.544 | 1.360 | 12 | 2.181 | 2.050 | 6 |
| 10 | 2.5 | 1.538 | 1.403 | 9 | 2.259 | 2.019 | 11 |
| 5 | 5.0 | 1.499 | 1.263 | 16 | 2.184 | 1.853 | 15 |
| 6 | 5.0 | 1.520 | 1.296 | 15 | 2.153 | 1.940 | 10 |
| 8 | 5.0 | 1.552 | 1.385 | 11 | 2.196 | 2.080 | 5 |
| 10 | 5.0 | 1.550 | 1.418 | 9 | 2.291 | 2.076 | 9 |
| 5 | 7.5 | 1.504 | 1.265 | 16 | 2.117 | 1.859 | 15 |
| 6 | 7.5 | 1.526 | 1.312 | 14 | 2.197 | 1.975 | 10 |
| 8 | 7.5 | 1.575 | 1.399 | 11 | 2.238 | 2.116 | 5 |
| 10 | 7.5 | 1.557 | 1.436 | 8 | 2.317 | 2.157 | 7 | regions providing different axial x-ray attenuations and sharpening a dose profile at a periphery of the collimated beam at a treatment plane spaced from the filter plate in a direction of x-ray propagation.

2. The sharpening filter of claim 1 wherein the sharpening provides an increased rate of drop-off of the dose profile at the periphery of collimated beam as one moves from the axis radially outward along the treatment plane in comparison to an un-sharpened collimated dose profile produced by a same x-ray generator and collimator without the filter plate.

3. The sharpening filter of claim 2 wherein the collimated beam provides an 80%-20% penumbra of no less than five percent smaller than a penumbra of the un-sharpened collimated beam.

4. The sharpening filter of claim 1 wherein the at least first and second circular attenuation regions have a radial thickness of no less than 0.5 millimeters.

5. The sharpening filter of claim 1 wherein the filter plate provides less than four concentric circular attenuation regions each having different axial x-ray attenuations.

6. The sharpening filter of claim 1 wherein the at least first and second circular attenuation regions include a central region providing a cylinder of attenuating material.

7. The sharpening tilter of claim 1 wherein the collimator produces a collimated beam having a diameter of less than 15 millimeters.

8. The sharpening filter of claim 1 wherein the treatment plane is at least 2.5 centimeters from the filter.

9. The sharpening filter of claim 1 wherein the filter is composed of metal or a metal composite.

10. The sharpening filter of claim 9 wherein the metal is tungsten.

11. The sharpening filter of claim 1 wherein the filter is attached at the outlet of collimator.

12. The sharpening filter of claim 1 wherein the filter has an axial thickness of less than five-millimeters.

13. The sharpening filter of claim 1 wherein the orthovoltage is in a range of 200-500 thousand electron volts peak potential.

14. An orthovoltage x-ray machine comprising:
 a housing supportable by a gantry arm for positioning with respect to a phantom, target, or patient;
 an x-ray source supported by the housing generating orthovoltage x-rays along an axis with respect to the housing;
 a collimator positioned with respect to the x-ray source providing a central channel extending along an axis between an inlet and an outlet, the collimator receiving x-rays from an x-ray source at the inlet and collimating those x-rays to into a collimated beam; and
 a filter plate positioned within the collimated beam providing at least a first and second circular attenuation region within the collimated beam and concentric about the axis, the at least first and second circular attenuation regions providing different axial x-ray attenuations and sharpening a periphery of the collimated beam at a treatment plane spaced from the filter plate in a direction of x-ray propagation;
 wherein the orthovoltage x-rays have an energy in a range of 200-500 thousand electron volts peak potential.

15. A kit of sharpening filters for orthovoltage x-rays comprising:
 a set of collimators each providing a central channel having a different diameter and extending along an axis between an inlet and an outlet, the collimator receiving x-rays from an orthovoltage x-ray source at the inlet and collimating those x-rays into a collimated beam; and
 a set of filter plates replaceably fitting in ones of the set of collimators within the collimated beam providing at least a first and second circular attenuation region within the collimated beam and concentric about the axis, the at least first and second circular attenuation regions providing different axial x-ray attenuations and sharpening the periphery of the collimated beam at a treatment plane spaced from the filter plate in a direction of x-ray propagation;
 wherein the set of collimator's and filter plates inter-fit to provide a range of different collimated beam diameters with different filter-to-treatment area distances.

16. The kit of claim 15 wherein the different collimated beam sizes include multiple collimated beam sizes in a range between five and 10 millimeters in diameter and different irradiation depths within a range of 2.5 to 7.5 centimeters.

17. A method of designing a sharpening filter for orthovoltage x-rays comprising the steps of:
 (a) employing a genetic algorithm subject to a set of predetermined filter design constraints to generate a set of potential filters providing at least a first and second circular attenuation region within a diameter of a collimated beam to be filtered and concentric about an axis of a propagation of the x-rays of the collimated beam, the at least first and second circular attenuation regions providing different axial x-ray attenuations and sharpening a periphery of the collimated beam at a treatment plane spaced from the filter plate in a direction of x-ray propagation;
 (b) modeling the collimated beams produced by each of the set of potential filters at the treatment plane;
 (c) assessing the fitness of each of the collimated beams according to a desired sharpness of the collimated beams at a treatment plane;
 (d) returning the fitness information to the genetic algorithm to produce a new set of filter designs combining features of filters producing the collimated beams with greatest fitness; and
 (e) repeating steps (a)-(d) for multiple iterations to produce at least one filter design providing improved sharpness.

18. The method of claim 17 wherein step (c) further assesses the fitness of each collimated beam according to the fluence of each pencil beam.

* * * * *